(12) United States Patent
Chen et al.

(10) Patent No.: US 11,017,535 B2
(45) Date of Patent: May 25, 2021

(54) METHOD AND SYSTEM FOR HYBRID MESH SEGMENTATION

(71) Applicant: Carestream Dental Technology Topco Limited, London (GB)

(72) Inventors: Shoupu Chen, Rochester, NY (US); Wei Ye, Shanghai (CN); Delphine Reynard, Montreuil (FR); Xavier Ripoche, Mandres les Roses (FR); Carl R. Wesolowski, Milton, GA (US)

( * ) Notice: Subject to any disclaimer, the term of this patent is extended or adjusted under 35 U.S.C. 154(b) by 0 days.

(21) Appl. No.: 16/328,065

(22) PCT Filed: Sep. 12, 2016

(86) PCT No.: PCT/US2016/051238
§ 371 (c)(1),
(2) Date: Feb. 25, 2019

(87) PCT Pub. No.: WO2018/038748
PCT Pub. Date: Mar. 1, 2018

(65) Prior Publication Data
US 2019/0197691 A1    Jun. 27, 2019

Related U.S. Application Data

(60) Provisional application No. 62/378,916, filed on Aug. 24, 2016.

(51) Int. Cl.
*G06T 7/11* (2017.01)
*A61C 9/00* (2006.01)
(Continued)

(52) U.S. Cl.
CPC ............ *G06T 7/11* (2017.01); *A61B 1/00045* (2013.01); *A61B 1/24* (2013.01); *A61C 9/006* (2013.01);
(Continued)

(58) Field of Classification Search
CPC . G06T 7/11; G06T 17/20; G06T 17/10; G06T 7/149; A61C 9/006; A61B 1/24
(Continued)

(56) References Cited

U.S. PATENT DOCUMENTS

| | | | |
|---|---|---|---|
| 9,261,356 B2 * | 2/2016 | Lampert | G01B 11/24 |
| 2009/0316966 A1 * | 12/2009 | Marshall | A61B 6/5217 |
| | | | 382/128 |

(Continued)

*Primary Examiner* — Congvan Tran

(57) ABSTRACT

A computer-implemented method for generating one or more segmented 3-D teeth models obtains a 3-D mesh model of a patient's dentition and executes a first segmentation procedure on the obtained 3-D mesh model, displaying one or more segmented teeth from the 3-D mesh model. At least one of the one or more segmented teeth is recorded according to operator instruction and removed from the 3-D mesh model to form a modified 3-D mesh model. A repeating sequence identifies a modified segmentation procedure, executes the modified segmentation procedure on the modified 3-D mesh model, displays one or more segmented teeth from the modified 3-D mesh model, records at least one of the one or more segmented teeth, and removes the recorded at least one tooth from the modified 3-D mesh model. Recorded segmentation results are displayed, stored, or transmitted.

15 Claims, 18 Drawing Sheets

(51) Int. Cl.
  *G06T 7/149* (2017.01)
  *G06T 7/10* (2017.01)
  *G06T 7/521* (2017.01)
  *A61B 1/00* (2006.01)
  *A61B 1/24* (2006.01)
  *G06T 17/10* (2006.01)
  *G06T 17/20* (2006.01)
  *A61C 7/00* (2006.01)

(52) U.S. Cl.
  CPC ............... *G06T 7/10* (2017.01); *G06T 7/149* (2017.01); *G06T 7/521* (2017.01); *G06T 17/10* (2013.01); *G06T 17/20* (2013.01); *A61C 2007/004* (2013.01); *G06T 2207/10028* (2013.01); *G06T 2207/20101* (2013.01); *G06T 2207/20116* (2013.01); *G06T 2207/20152* (2013.01); *G06T 2207/20156* (2013.01); *G06T 2207/30036* (2013.01); *G06T 2210/41* (2013.01); *G06T 2219/2008* (2013.01)

(58) Field of Classification Search
  USPC ........................................................ 382/154
  See application file for complete search history.

(56) References Cited

U.S. PATENT DOCUMENTS

| | | | |
|---|---|---|---|
| 2015/0173855 A1* | 6/2015 | Sporbert | A61C 7/00 703/1 |
| 2016/0220200 A1* | 8/2016 | Sandholm | A61B 5/7246 |
| 2016/0317250 A1* | 11/2016 | Sachdeva | A61B 5/0088 |

* cited by examiner

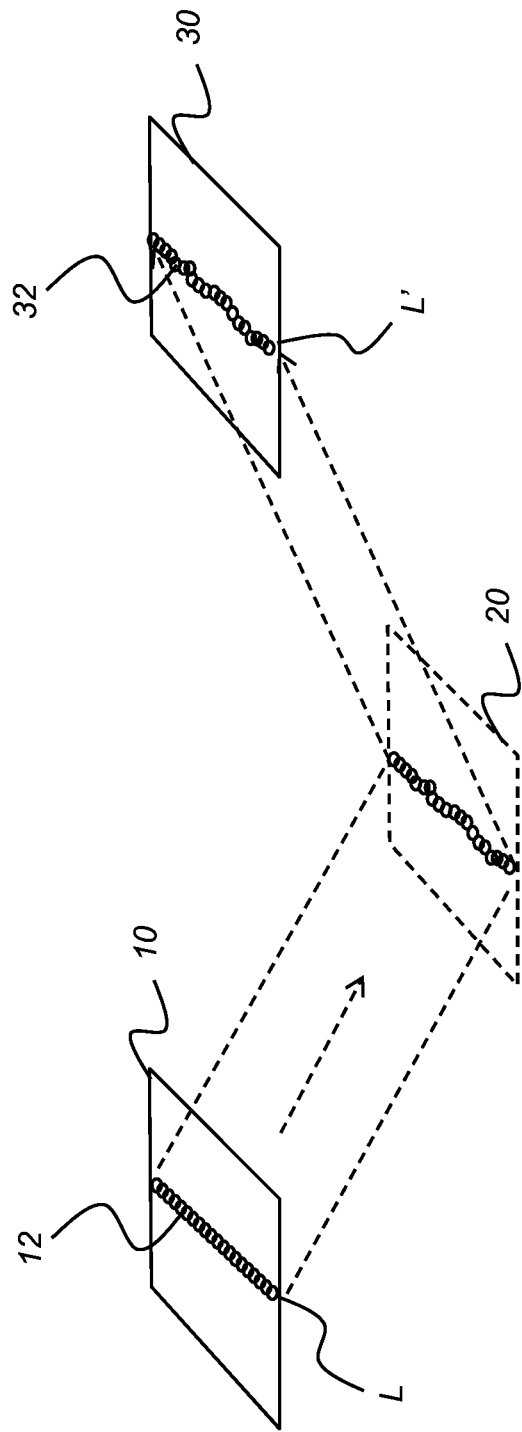

METHOD AND SYSTEM FOR HYBRID MESH SEGMENTATION

TECHNICAL FIELD

The disclosure relates generally to segmentation of elements that are represented by a three-dimensional mesh and more particularly to methods and apparatus for automated tooth segmentation in a contour image.

BACKGROUND

Three-dimensional (3-D) imaging and 3-D image processing are areas of growing interest to dental/orthodontic practitioners for computer-aided diagnosis and overall improved patient care. In the field of cephalometric analysis, 3-D imaging and 3-D image processing offer significant advantages in terms of flexibility, accuracy, and repeatability. 3-D cephalometric analysis overcomes some of the shortcomings associated with conventional methods of two-dimensional (2-D) cephalometric analysis, such as 2-D geometric errors of perspective projection, magnification, and head positioning in projection, for example. 3-D cephalometrics has been shown to yield objective data that is more accurate, since it is based on calculation rather than being largely dependent upon discrete measurements, as is the case with 2-D cephalometrics.

Early research using 3-D cephalometrics methods employed 3-D imaging and parametric analysis of maxillofacial anatomical structures using cone beam computed tomography (CBCT) of a patient's head. Using CBCT methods, a significant role of the 3-D cephalometric analysis was to define mathematical models of maxillary and mandibular arches for which the axes of inertia were calculated for each tooth or group of teeth. This, in turn, required the segmentation of individual teeth from the acquired CBCT head volume of a patient.

Conventionally, during an orthodontic treatment procedure, multiple 2-D X-ray cephalogram acquisitions are used to assess treatment progress. Conventional 3-D cephalometric analysis can also be used for this purpose, requiring multiple CBCT scans. However, both 2-D and 3-D radiographic imaging methods expose the patient to ionizing radiation. Reducing overall patient exposure to radiation is desirable, particularly for younger patients.

Optical intraoral scans, in general, produce contours of dentition objects and have been helpful in improving visualization of teeth, gums, and other intra-oral structures. Surface contour information can be particularly useful for assessment of tooth condition and has recognized value for various types of dental procedures, such as for restorative dentistry. This can provide a valuable tool to assist the dental practitioner in identifying various problems and in validating other measurements and observations related to the patient's teeth and supporting structures. Surface contour information can also be used to generate 3-D models of dentition components such as individual teeth; the position and orientation information related to individual teeth can then be used in assessing orthodontic treatment progress. With proper use of surface contour imaging, the need for multiple 2-D or 3-D X-ray acquisitions of a patient's dentition can be avoided.

A number of techniques have been developed for obtaining surface contour information from various types of objects in medical, industrial, and other applications. Optical 3-dimensional (3-D) measurement methods provide shape and spatial information using light directed onto a surface in various ways. Among types of imaging methods used for contour imaging are fringe projection devices. Fringe projection imaging uses patterned or structured light and camera/sensor triangulation to obtain surface contour information for structures of various types. Once the fringe projection images are processed, a point cloud can be generated. A mesh can then be formed from the point cloud or a plurality of point clouds, in order to reconstruct at least a planar approximation to the surface.

Mesh representation can be particularly useful for showing surface structure of teeth and gums and can be obtained using a handheld camera and without requiring harmful radiation levels. However, when using conventional image processing approaches, mesh representation has been found to lack some of the inherent versatility and utility that is available using cone-beam computed tomography (CBCT) or other techniques that expose the patient to radiation. One area in which mesh representation has yielded only disappointing results relates to segmentation. Segmentation allows the practitioner to identify and isolate the crown and other visible portions of the tooth from gums and related supporting structure. Conventional methods for segmentation of mesh images can often be inaccurate and may fail to distinguish tooth structure from supporting tissues.

Various approaches for addressing the segmentation problem for mesh images have been proposed, such as the following:

(i) A method described in the article "Snake-Based Segmentation of Teeth from Virtual Dental Casts" by Thomas Kronfeld et al. (in Computer-Aided Design & applications, 7 (a), 2010) employs an active contour segmentation method that attempts to separate every tooth and gum surface in a single processing iteration. The approach that is described, however, is not a topology-independent method and can fail, particularly where there are missing teeth in the jaw mesh.

(ii) An article entitled "Perception-based 3D Triangle Mesh Segmentation Using Fast Marching Watershed" by Page, D. L. et al. (in *Proc. CVPI* vol II 2003) describes using a Fast Marching Watershed method for mesh segmentation. The Fast Marching Watershed method that is described requires the user to manually enter seed points. The seed points must be placed at both sides of the contours of the regions under segmentation. The method then attempts to segment all regions in one step, using seed information. For jaw mesh segmentation, this type of method segments each tooth as well as the gum at the same time. This makes the method less desirable, because segmenting teeth from the gum region typically requires parameters and processing that differ from those needed for the task of segmenting teeth from each other. Using different segmentation strategies for different types of dentition components with alternate segmentation requirements would provide better performance.

(iii) For support of his thesis. "Evaluation of software developed for automated segmentation of digital dental models", J. M. Moon used a software tool that decomposed the segmentation process into two steps: separation of teeth from gingival structure and segmentation of whole arch structure into individual tooth objects. The software tool used in Moon's thesis finds maximum curvature in the mesh and requires the user to manually choose a curvature threshold to obtain margin vertices that are used for segmenting the tooth. The software also requires the user to manually edit margins in order to remove erroneous segmentation results.

Directed to analysis of shape and positional characteristics, this software tool does not consider employing color information in the separation of teeth regions from the gum regions.

(iv) U.S. Patent application 20030039389 A1 entitled "Manipulation a digital dentition model to form models of individual dentition components" by Jones, T. N. et al. disclose a method of separating portions of the dentition model representing the adjacent teeth.

Each of these segmentation approach has its strengths and weaknesses for automating the segmentation process. Some teeth are readily identified and can be segmented with high accuracy using snake-based segmentation, for example. However, this same segmentation routine may perform poorly for teeth of different shapes or positioned differently within the same dental arch.

Because different segmentation routines work well but vary in performance based on tooth shape, size, position, and other characteristics, no one segmentation approach can be optimized for all teeth or for all situations. Thus, it can be seen that there would be advantages to a flexible approach for applying tooth segmentation. There is, then, a need for improved methods for segmentation of mesh representation of dentition.

SUMMARY

An aspect of this application is to advance the art of tooth segmentation in relation to volume imaging and visualization used in medical and dental applications.

Another aspect of this application is to address, in whole or in part, at least the foregoing and other deficiencies in the related art.

It is another aspect of this application to provide, in whole or in part, at least the advantages described herein.

Method and/or apparatus embodiments according to the present disclosure can allow the viewer to have the advantages of automated segmentation as well as the capability to interact with partially automated or manual segmentation processing in order to help provide progressively improved results.

These objects are given only by way of illustrative example, and such objects may be exemplary of one or more embodiments of the invention. Other desirable objectives and advantages inherently achieved in the present disclosure may occur or become apparent to those skilled in the art. The invention is defined by the appended claims.

According to one aspect of the disclosure, there is provided a computer-implemented method for generating one or more segmented 3-D teeth models, that can include obtaining a 3-D mesh model of a patient's dentition, executing a first segmentation procedure on the obtained 3-D mesh model and displaying one or more segmented teeth from the 3-D mesh model, recording at least one of the one or more segmented teeth according to operator instruction and removing the recorded at least one tooth from the 3-D mesh model to form a modified 3-D mesh model, repeating, one or more times, a sequence of (i) identifying a modified segmentation procedure; (ii) executing the modified segmentation procedure on the modified 3-D mesh model and displaying one or more segmented teeth from the modified 3-D mesh model; (iii) recording at least one of the one or more segmented teeth and removing the recorded at least one tooth from the modified 3-D mesh model, and displaying, storing, or transmitting recorded segmentation results.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2 shows schematically how patterned light is used for obtaining surface contour information using a handheld camera or other portable imaging device.

DETAILED DESCRIPTION OF EXEMPLARY EMBODIMENTS

Figure 1:
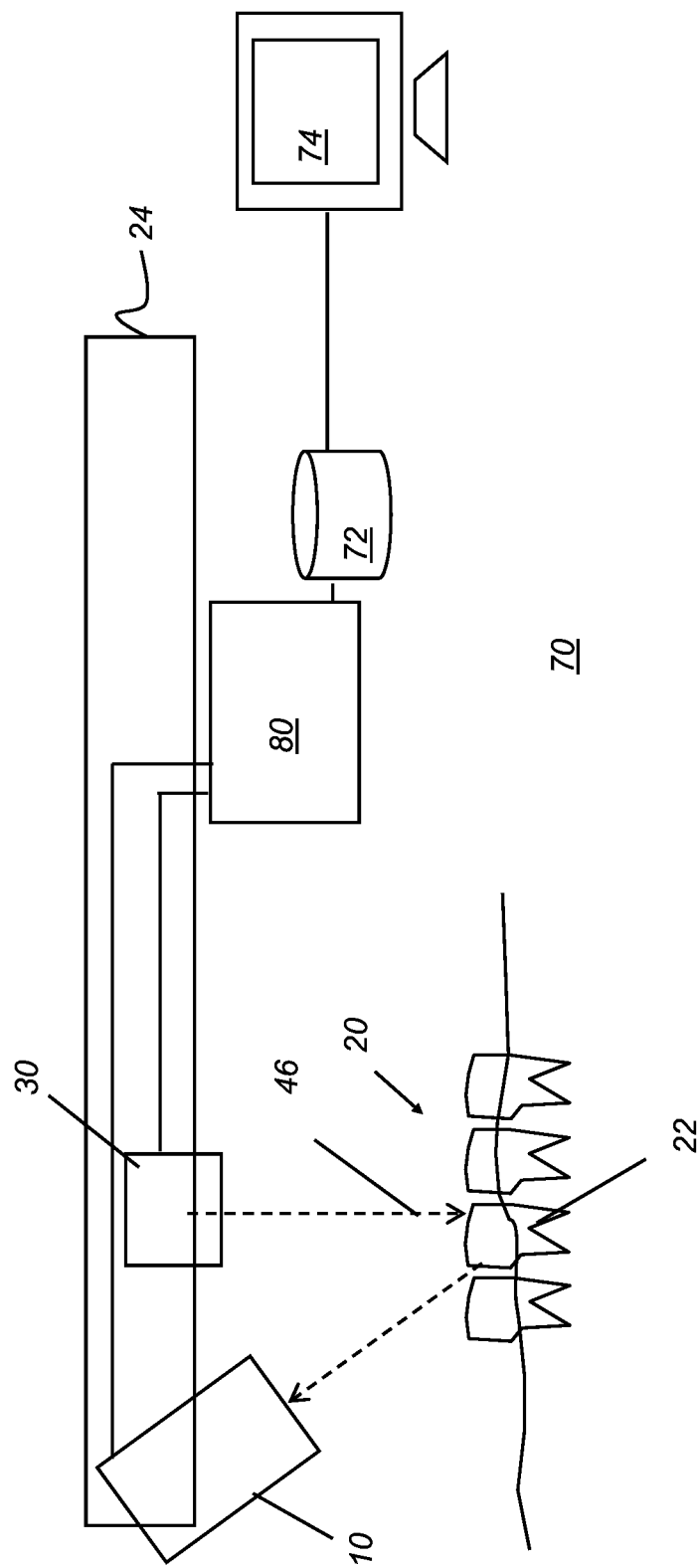
FIG. 1 is a schematic diagram that shows components of an imaging apparatus for surface contour imaging of a patient's teeth and related structures.

This application claims the benefit of U.S. Provisional application U.S. Ser. No. 62/378,916, provisionally filed on Aug. 24, 2016, entitled "METHOD AND SYSTEM FOR HYBRID MESH SEGMENTATION", in the name of Shoupu Chen et al., which is incorporated herein by reference in its entirety.

The following is a detailed description of exemplary embodiments, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

The term "exemplary" indicates that the description is used as an example, rather than implying that it is an ideal.

The term "in signal communication" as used in the application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional or volume images and a pixel for 2-dimensional (2-D) images. For the purposes of the description herein, the terms voxel and pixel can generally be considered equivalent, describing an image elemental datum that is capable of having a range of numerical values. Voxels and pixels have attributes of both spatial location and image data code value.

"Patterned light" is used to indicate light that has a predetermined spatial pattern, such that the light has one or more features such as one or more discernable parallel lines, curves, a grid or checkerboard pattern, or other features having areas of light separated by areas without illumination. In the context of the present disclosure, the phrases "patterned light" and "structured light" are considered to be equivalent, both used to identify the light that is projected toward a subject in order to derive contour image data.

In the context of the present disclosure, the terms "viewer", "operator", and "user" are considered to be equivalent and refer to the viewing practitioner, technician, or other person who can view and manipulate a contour image that is formed from a combination of multiple structured light images on a display monitor. For segmentation processing, for example, the viewer is likely a dental practitioner.

A "viewer instruction". "operator instruction", or "operator command" can be obtained from explicit commands entered by the viewer or may be implicitly obtained or derived based on some other user action, such as making an equipment setting, for example. With respect to entries entered on an operator interface, such as an interface using a display monitor and keyboard, for example, the terms "command" and "instruction" may be used interchangeably to refer to an operator entry.

In the context of the present disclosure, a single projected line of light is considered a "one dimensional" pattern, since the line has an almost negligible width, such as when projected from a line laser, and has a length that is its predominant dimension. Two or more of such lines projected side by side, either simultaneously or in a scanned arrangement, provide a simple two-dimensional pattern. In exemplary embodiments, lines of light can be linear, curved or three-dimensional. This projected pattern can be used to characterize the surface features of a tooth or other anatomical structure.

The terms "3-D model", "point cloud", "3-D surface", and "mesh" may be used synonymously in the context of the present disclosure. The dense point cloud is formed using techniques familiar to those skilled in the volume imaging arts for forming a point cloud and relates generally to methods that identify, from the point cloud, vertex points corresponding to surface features. The dense point cloud is thus generated using the reconstructed contour data from one or more reflectance images. Dense point cloud information serves as the basis for a polygon model or mesh at high density for the teeth and gum surfaces.

According to the present disclosure, the phrase "geometric primitive" refers to basic 2-D geometric shapes that can be entered by the operator in order to indicate areas of an image. By way of example, and not limitation, geometric primitives can include lines, curves, points, and other open shapes, as well as closed shapes that can be formed by the operator, such as circles, closed curves, rectangles and squares, polygons, and the like.

Embodiments of the present disclosure provide exemplary methods and/or apparatus that can help to eliminate the need for multiple CBCT scans for visualization of tooth and jaw structures. Exemplary methods and/or apparatus embodiments can be used to combine a single CBCT volume with optical intraoral scans that have the capability of tracking the root position at various stages of orthodontic treatment, for example. To achieve this, the intraoral scans are segmented so that exposed portions, such as individual tooth crowns, from the intraoral scan can be aligned with the individual tooth and root structure segmented from the CBCT volume.

FIG. 1 is a schematic diagram showing an imaging apparatus 70 for projecting and imaging using structured light patterns 46. Imaging apparatus 70 uses a handheld camera 24 for image acquisition according to an embodiment of the present disclosure. A control logic processor 80, or other type of computer that may be part of camera 24 controls the operation of an illumination array 10 that generates the structured light and controls operation of an imaging sensor array 30. Image data from surface 20, such as from a tooth 22, is obtained from imaging sensor array 30 and stored in a memory 72. Control logic processor 80, in signal communication with camera 24 components that acquire the image, processes the received image data and stores the mapping in memory 72. The resulting image from memory 72 is then optionally rendered and displayed on a display 74. Memory 72 may also include a display buffer for temporarily storing display 74 image content.

In fringe projection imaging of a surface, a pattern of lines is projected from illumination array 10 toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of fringe projection imaging, used in order to complete the contour mapping of the surface and to increase overall resolution in the contour image.

The schematic diagram of FIG. 2 shows, with the example of a single line of light L, how patterned light is used for obtaining surface contour information using a handheld camera or other portable imaging device. A mapping is obtained as an illumination array 10 directs a pattern of light onto a surface 20 and a corresponding image of a line L' is formed on an imaging sensor array 30. Each pixel 32 on imaging sensor array 30 maps to a corresponding pixel 12 on illumination array 10 according to modulation by surface 20. Shifts in pixel position, as represented in FIG. 2, yield useful information about the contour of surface 20. It can be appreciated that the basic pattern shown in FIG. 2 can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the light pattern as needed for the mapping sequence.

By projecting and capturing images that show structured light patterns that duplicate the arrangement shown in FIGS. 1 and 2 multiple times, the image of the contour line on the camera simultaneously locates a number of surface points of the imaged object. This can speed the process of gathering many sample points, while the plane of light (and usually also the receiving camera) is laterally moved in order to "paint" some or all of the exterior surface of the object with the plane of light.

Figure 3:
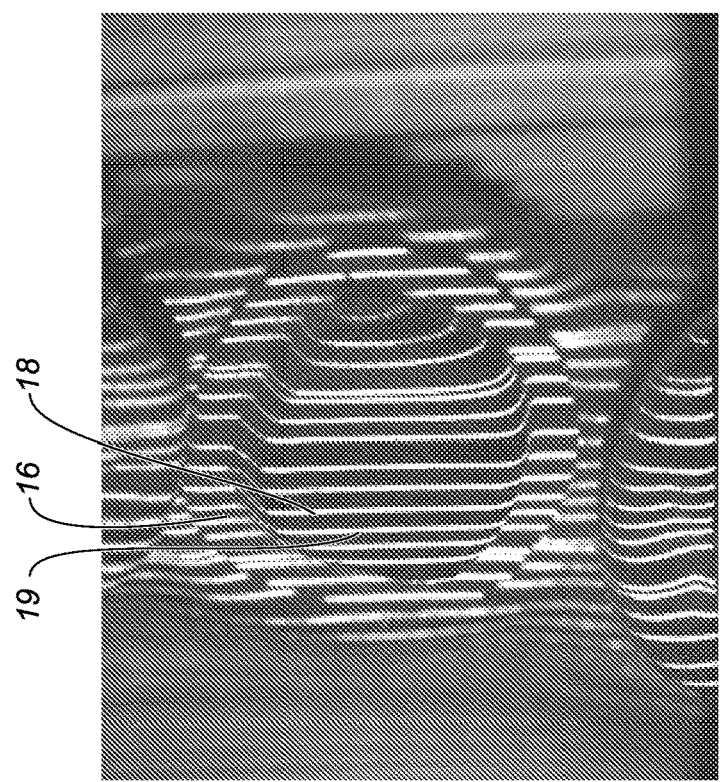
FIG. 3 shows an example of surface imaging using a pattern with multiple lines of light.

FIG. 3 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult to determine whether line segment 16 is from the same line of illumination as line segment 18 or adjacent line segment 19.

Figure 4:
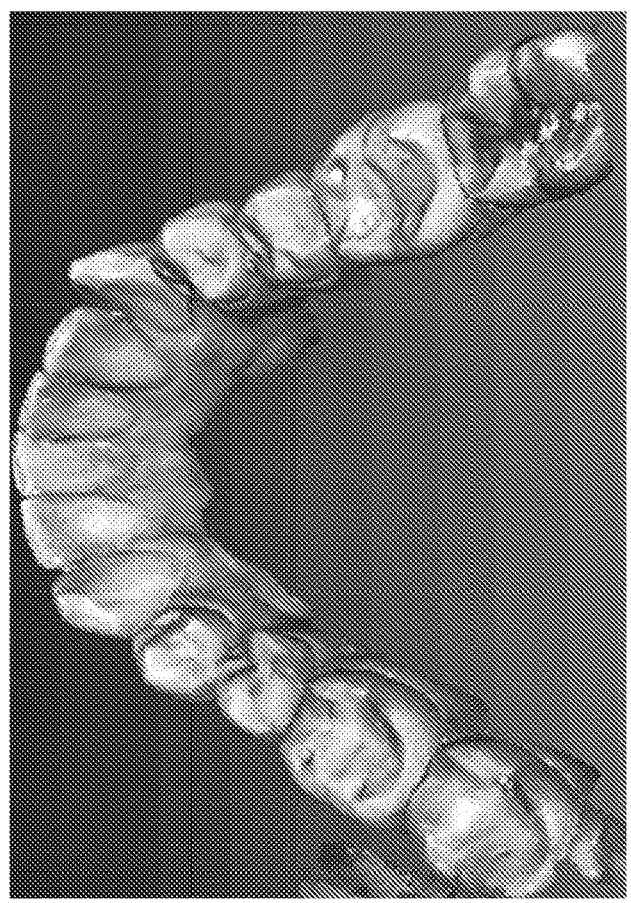
FIG. 4 shows a point cloud generated from structured light imaging, such as that shown in FIG. 3.

By knowing the instantaneous position of the camera and the instantaneous position of the line of light within an object-relative coordinate system when the image was acquired, a computer and software can use triangulation methods to compute the coordinates of numerous illuminated surface points. As the plane is moved to intersect eventually with some or all of the surface of the object, the coordinates of an increasing number of points are accumulated. As a result of this image acquisition, a point cloud of vertex points or vertices can be identified and used to represent the extent of a surface within a volume. By way of example, FIG. 4 shows a dense point cloud 50 generated from a structured light imaging apparatus, CS 3500 3-D camera made by Carestream Health, Inc., Rochester N.Y., USA, using results from patterned illumination such as that shown in FIG. 3. The point cloud 50 models physical location of sampled points on tooth surfaces and other intraoral surfaces or, more generally, of surfaces of a real-world object. Variable resolution can be obtained. The example of FIG. 4 shows an exemplary 100 micron resolution. The points in the point cloud represent actual, measured points on the three dimensional surface of an object.

The surface structure can be approximated from the point cloud representation by forming a polygon mesh, in which adjacent vertices are connected by line segments. For a vertex, its adjacent vertices are those vertices closest to the vertex in terms of Euclidean distance.

Figure 5:
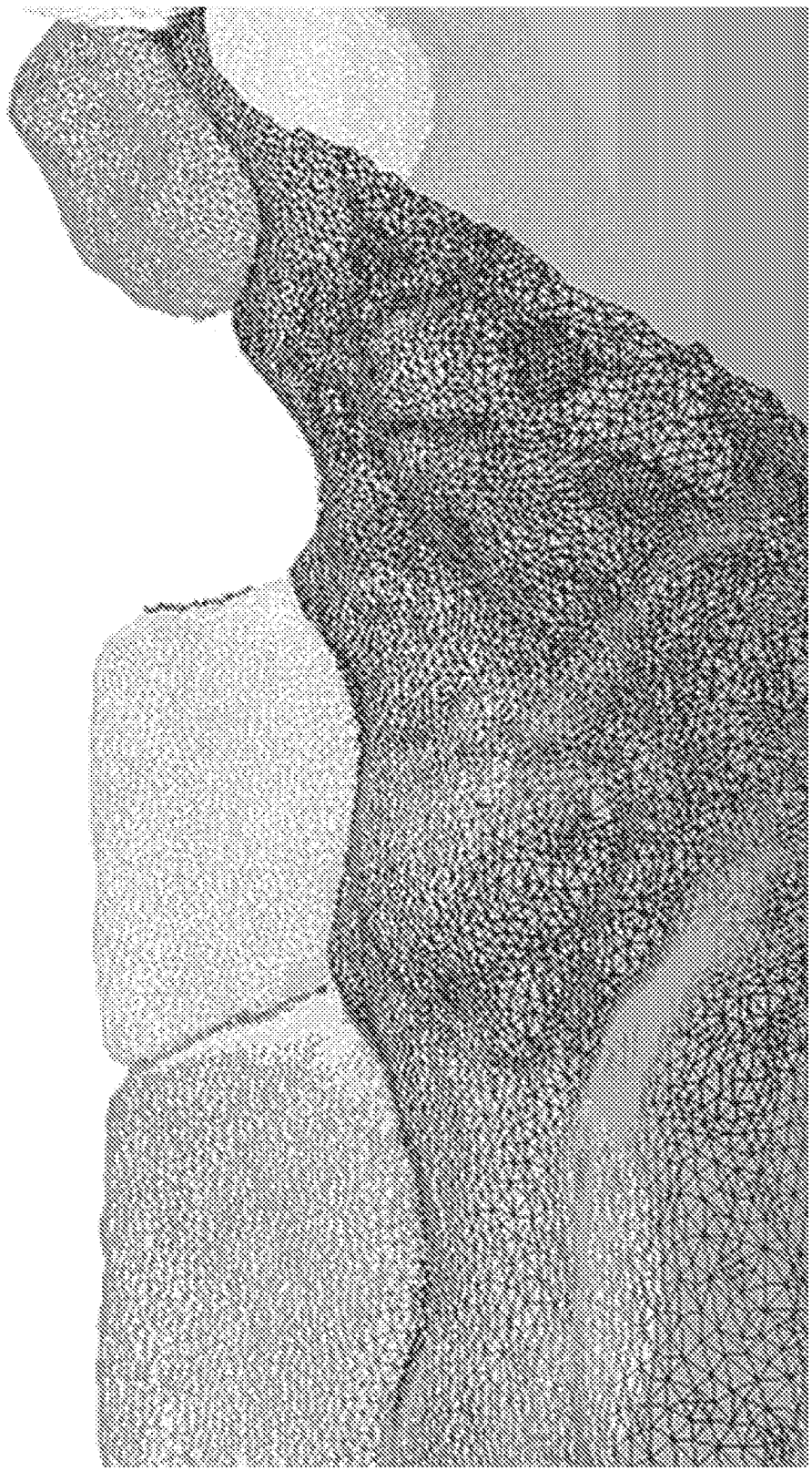
FIG. 5 shows a polygon mesh 60 in the simple form of a triangular mesh.

By way of example, FIG. 5 shows a 3-D polygon mesh model 60 in the simple form of a triangular mesh. A triangular mesh forms a basic mesh structure that can be generated from a point cloud and used as a digital model to represent a 3-D object by its approximate surface shape, in the form of triangular plane segments sharing adjacent boundaries. Methods/apparatus for forming a polygon mesh model, such as a triangular mesh or more complex mesh structure, are well known to those skilled in the contour imaging arts. The polygon unit of the mesh model, and relationships between neighboring polygons, can be used in embodiments of the present disclosure to extract features (e.g., curvatures, minimum curvatures, edges, spatial relations, etc.) at the teeth boundaries.

In intra-oral imaging, segmentation of individual components of the image content from a digital model can be of value to the dental practitioner in various procedures, including orthodontic treatment and preparation of crowns, implants, and other prosthetic devices, for example. Various methods have been proposed and demonstrated for mesh-based segmentation of teeth from gums and of teeth from each other. However, drawbacks of conventional segmentation solutions include requirements for a significant level of operator skill and a high degree of computational complexity. Conventional approaches to the problem of segmenting tooth components and other dentition features have yielded disappointing results in many cases. Exemplary method and/or apparatus embodiments according to the present disclosure address such problems with segmentation that can utilize the polygonal mesh data as a type of source digital model and can operate in more than one stage: e.g., first, performing an automated segmentation algorithm/procedures that can provide at least a close or coarse approximation of the needed segmentation of the digital model; and second, allowing operator interactions to improve, correct and/or clean up observed errors and inconsistencies in the automated results, which can yield highly accurate results that are difficult to achieve in a purely automated manner, but not placing significant requirements on operator time or skill level and/or on needed computer resources. This hybrid approach in exemplary method and/or apparatus embodiments can help to combine computing and image processing power with operator perception to check, correct, and refine results of automated processing.

Figure 6A:
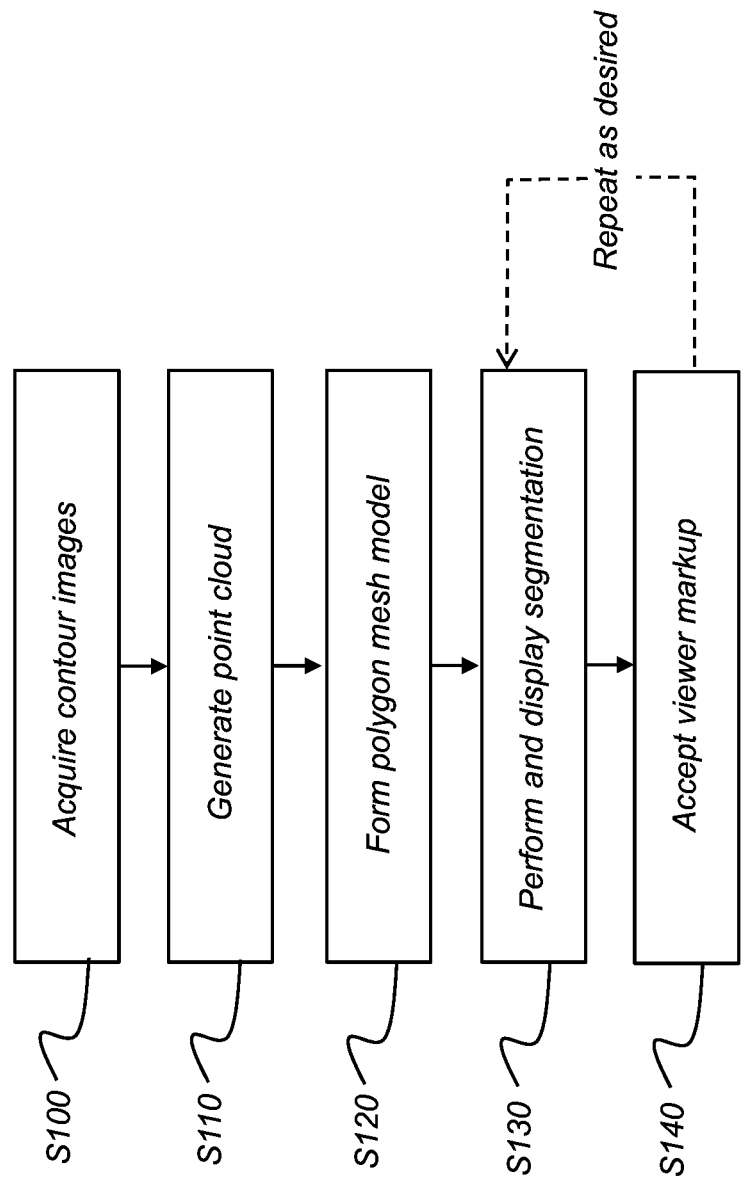
FIG. 6A is a logic flow diagram that shows a hybrid sequence for mesh segmentation according to an embodiment of the present disclosure.

The logic flow diagram of FIG. 6A shows a hybrid sequence for tooth mesh segmentation and generation of a digital model to identify individual features or intraoral components such as teeth from within the mouth according to an exemplary embodiment of the present disclosure. In an image acquisition step S100, a plurality of structured light images of the patient's dentition are captured, providing a set of contour images for processing. A point cloud generation step S110 then generates a point cloud of the patient's dentition using the set of contour images. A polygon mesh generation step S120 forms a polygon mesh by connecting adjacent points from the point cloud results. A triangular mesh provides one type of polygon mesh that can be readily generated for approximating a surface contour; more complex polygon mesh configurations can alternately be used.

Continuing with the FIG. 6A sequence, given the polygon mesh, a segmentation step S130 can be executed. For a dental contour image, for example, segmentation step S130 can distinguish teeth from gum tissue, as well as distinguishing one tooth from another. Segmentation results can then be displayed, showing the results of this initial, automated segmentation processing. The automated segmentation step S130 can provide an intermediate image. Thus automated step S130 can perform the bulk of segmentation processing, but can further benefit from operator review and refinements of results. For its automatic processing, segmentation step S130 can use any of a number of known segmentation techniques, such as fast-marching watershed algorithms, so-called snake-based segmentation, and other methods known to those skilled in the imaging arts, as noted earlier.

FIG. 6A also shows an optional repeat loop that can enable viewer interaction with the intermediate image for refining the results of the automated segmentation processing, for example, using the basic apparatus shown in FIG. 1. An accept operator instructions step S140 can be executed, during which the viewer indicates, on the displayed results, seed points, seed lines, block lines, boundary features, or other markings that identify one or more distinct features of the segmentation results to allow further segmentation refinement and processing. Viewer markup instructions cause segmentation step S130 to be executed at least a second time, this second time using input markup(s) from entered viewer instructions. It can be appreciated that different segmentation algorithms can be applied at various stages of automated or manual processing. Final results of segmentation processing can be displayed, stored, and transmitted between computers, such as over a wired or wireless network, for example.

The process shown in FIG. 6A can thus allow automated segmentation to perform the coarse segmentation (e.g., first segmentation) that can be more easily accomplished, such as segmentation of teeth from gum tissue, for example. Thus, for example, tooth and gum partitioning can be automated. In one embodiment, tooth and gum partitioning can use an automated curvature-based method that computes curvature of vertices in the mesh, and then uses a thresholding algorithm to identify margin vertices having large negative curvature. Alternately, color-based segmentation can be used for tooth segmentation from the gums. This type of method can obtain average hue values from regions of the image and calculate threshold values that partition image content.

Figure 6B:
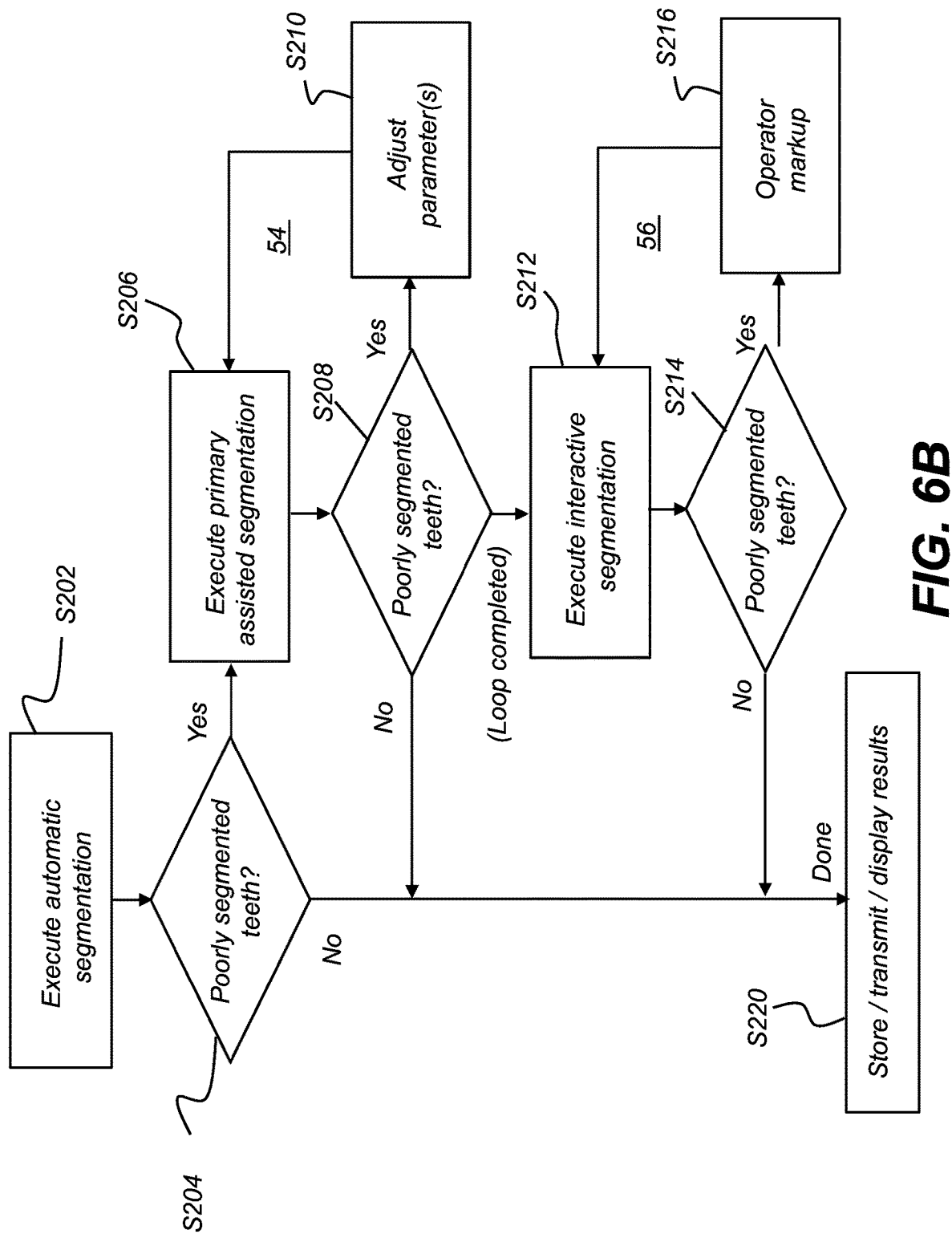
FIG. 6B is a logic flow diagram that shows a workflow sequence for hybrid segmentation of the tooth according to an embodiment of the present disclosure.
Figure 7B:
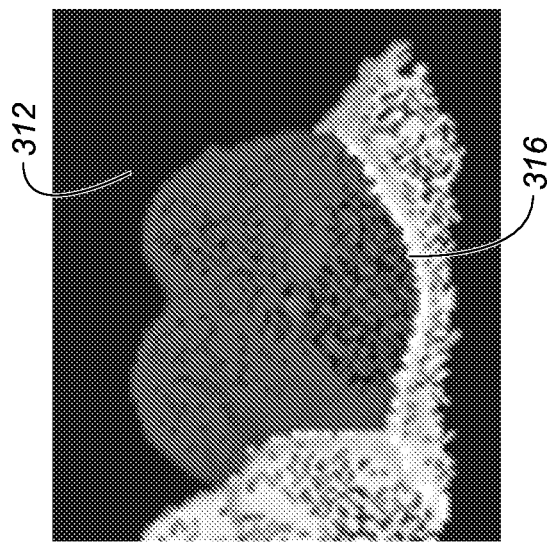
FIG. 7B shows an example of an improved segmentation.
Figure 7A:
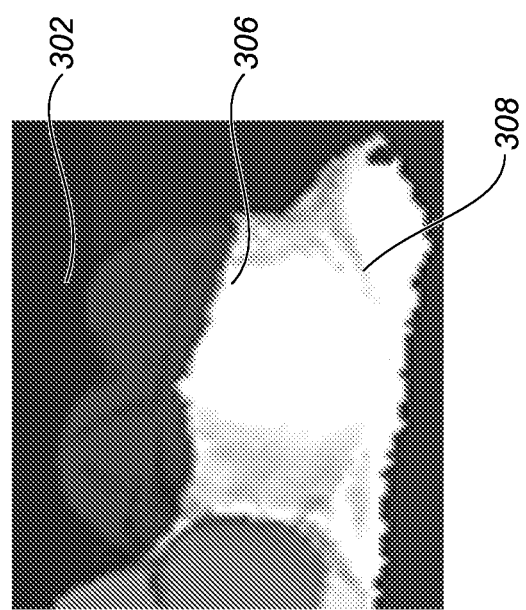
FIG. 7A shows an example of a poorly segmented tooth.

An exemplary embodiment of workflow for the hybrid tooth segmentation system is depicted in the logic flow diagram of FIG. 6B. Upon receiving a dentition mesh such as the one described in Step S120 and shown in FIGS. 4 and 5, the control logic processor 80 (FIG. 1) initiates an automated segmentation step S202 in which a fully automatic tooth segmentation tool is evoked to delineate teeth and gum regions and delineate individual teeth regions. The fully automatic tooth segmentation tool employs exemplary algorithms such as active contour models published in the literature or otherwise well-known to those skilled in the image processing arts. The delineation of teeth effectively produces individually segmented teeth; however, these generated teeth may contain poorly segmented intraoral components. A first checking step S204 then checks for poorly segmented intraoral components. Checking for incorrect or incomplete segmentation in step S204 can be accomplished either computationally, such as by applying trained artificial intelligence algorithms to the segmentation results, or by viewer interaction, such as following visual inspection by the viewer. By way of example, FIG. 7A shows an exemplary poorly segmented or mis-segmented tooth 302. As shown in FIG. 7A, a segmented tooth boundary 306 is not aligned with an actual tooth boundary 308.

Still referring to the workflow process in FIG. 6B, if checking Step S204 identifies one or more poorly segmented teeth, either computationally or visually, a primary assisted segmentation step S206 executes, activating a segmentation procedure that is also automated, but allows some level of operator adjustment. Primary assisted segmentation step S206 applies an algorithm for segmentation that allows operator adjustment of one or more parameters in a parameter adjustment step S210. Another checking step S208 executes to determine if additional segmentation processing is needed. The adjustable parameter can be altered computationally or explicitly by an operator instruction in step S210. Subsequent figures show an exemplary operator interface for parameter adjustment.

An exemplary algorithm employed in primary assisted segmentation Step S206 can be a well-known technique, such as the mesh minimum curvature-based segmentation method. The adjustable parameter can be the threshold value of the curvature. With the help of the parameter adjustment in step S210, a correction of the poorly segmented tooth can be made. FIG. 7B shows an image of tooth 312 that, by comparison with FIG. 7A, shows a segmented tooth boundary 316 now well aligned with the actual boundary.

Figure 8A:
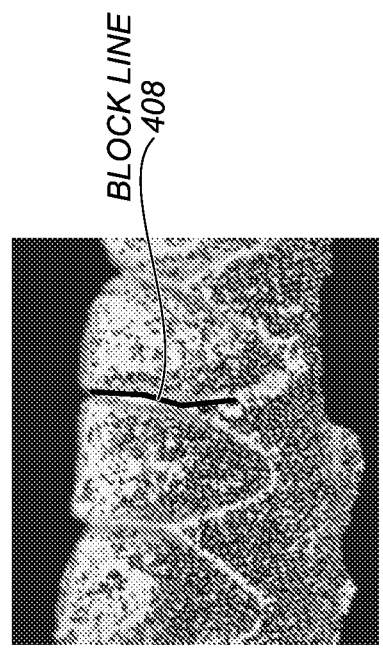
FIG. 8A shows an example of a seed line trace pattern.
Figure 8B:
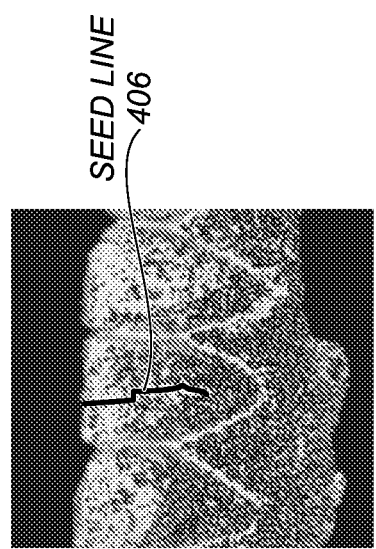
FIG. 8B shows an example of a block line trace pattern.

However, as is clear from the exemplary workflow embodiment shown in FIG. 6B, the delineation of teeth performed in Step S206 may still produce poorly segmented intraoral components or features, so that a repeated segmentation process is helpful. The checking of poor segmentation in step S208 can be accomplished either computationally, such as by applying artificial intelligence algorithms to the segmentation results, or more directly, by visual inspection performed by the user. In addition to the adjustable parameter adjusted in Step S210, the hybrid tooth segmentation system optionally allows the user to add exemplary geometric primitives such as seed lines on the tooth region and add blocking lines between the teeth or between the teeth and gum to aid the tooth segmentation process. FIG. 8A shows an exemplary seed line 406 for marking a tooth, added to a mesh image 62. FIG. 8B shows an exemplary block line 408 for indicating space between two teeth, added to a mesh image 62.

The three basic steps, Step S206, Step S208 and Step S210 in the FIG. 6B sequence constitute an exemplary primary segmentation loop 54 that follows the fully automatic segmentation of step S202 and checking step S204. This exemplary primary segmentation loop 54 is intended to correct segmentation errors from the fully automated segmentation of automated segmentation step S202, as identified in step S204. Exemplary primary segmentation loop 54 can be executed one or more times, as needed. When exemplary primary segmentation loop 54 is successful, segmentation can be complete.

In some cases, however, additional segmentation processing beyond what is provided by primary segmentation loop 54 is needed. Segmentation processing can be complicated by various factors, such as tooth crowding, irregular tooth shapes, artifacts from scanning, indistinct tooth contours, and undistinguishable interstices among others. Where additional segmentation is needed, an exemplary secondary segmentation loop 56 can be used to provide more interactive segmentation approaches. The secondary segmentation loop 56 can include an interactive segmentation step S212, another checking step S214, and an operator markup step S216. Interactive segmentation step S212 can activate a segmentation process that works with the operator for indicating areas of the image to be segmented from other areas. Interactive segmentation step S212 can have an automated sequence, implemented by an exemplary algorithm such as a "fast march" method known to those skilled in the image segmentation arts. Step S212 may require population of the tooth region images by operator-entered seeds or seed lines or other types of geometric primitives before activation or during processing. In certain exemplary embodiments, seed lines or other features can be automatically generated in Step S100, S110 and S120 when the dentition mesh is entered into the system for optional operator adjustment (e.g., subsequent operations such as secondary segmentation loop 56 or Step 212). In addition, the features, seeds or seed lines can be added to the segmentation process in operator markup Step S216 by the user. The results from Step S212 are subject to inspection by the user in Step S216. Results from the hybrid automated/interactive segmentation processing can then be displayed in a display step S220, as well as stored and transmitted to another computer.

Following the sequence of FIG. 6B, some exemplary methods/apparatus of the present disclosure provide a hybrid tooth segmentation that provides the benefits of interactive segmentation with human-machine synergy.

Figure 9A:
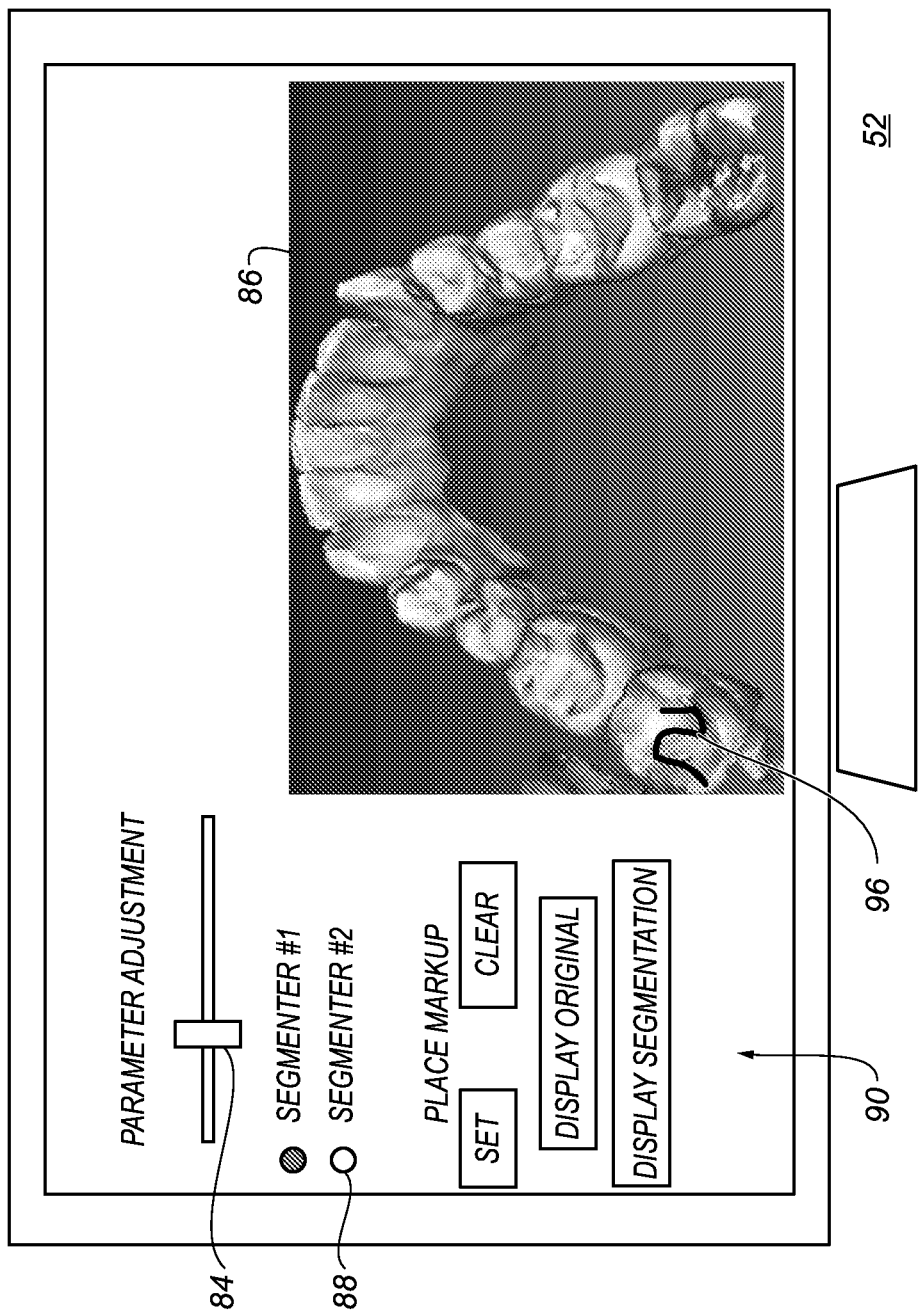
FIGS. 9A, 9B and 9C show operator interface screens for review and entry of markup instructions for refining tooth mesh segmentation processing according to certain embodiments of the present disclosure.
Figure 9B:
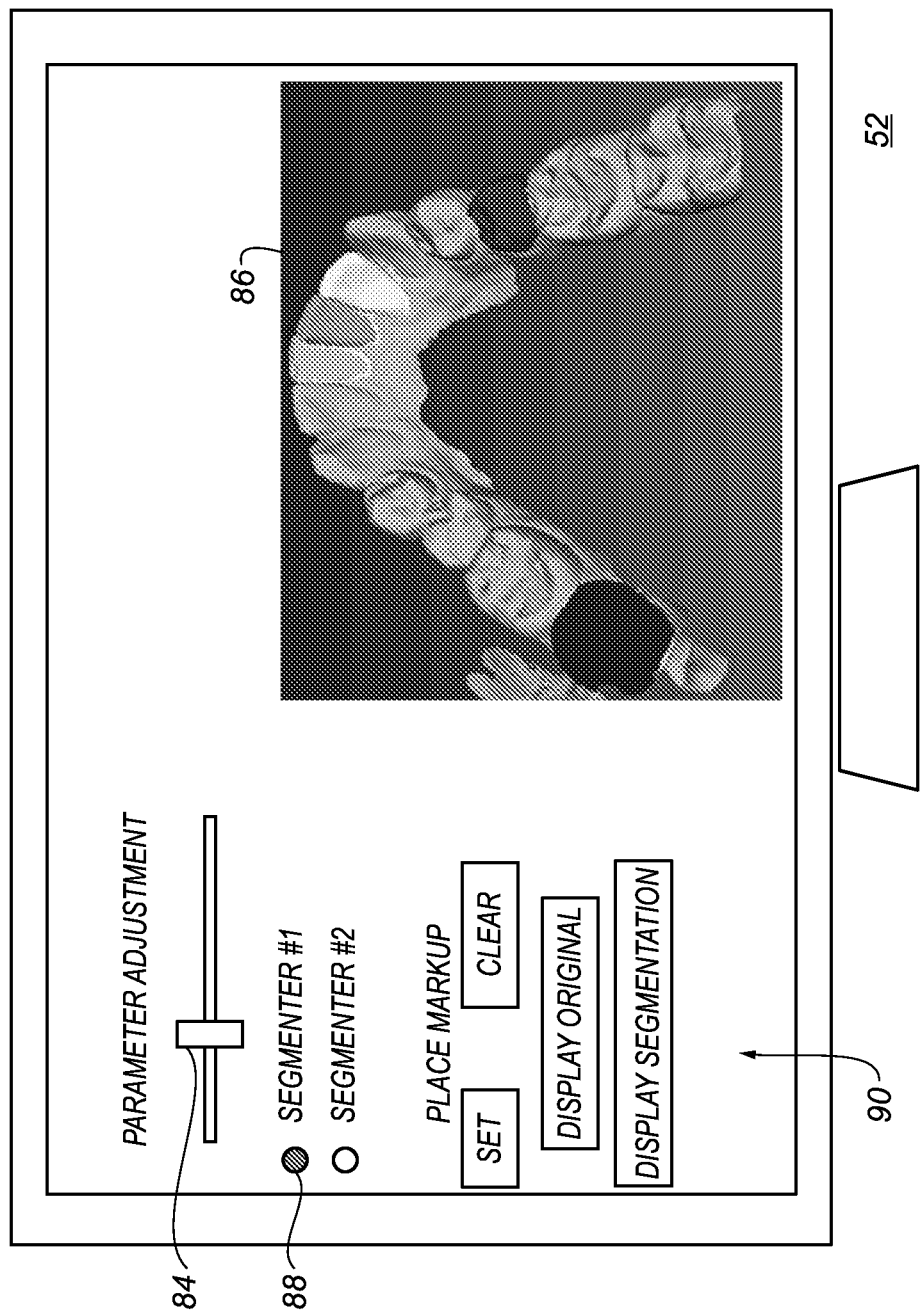
Figure 9C:
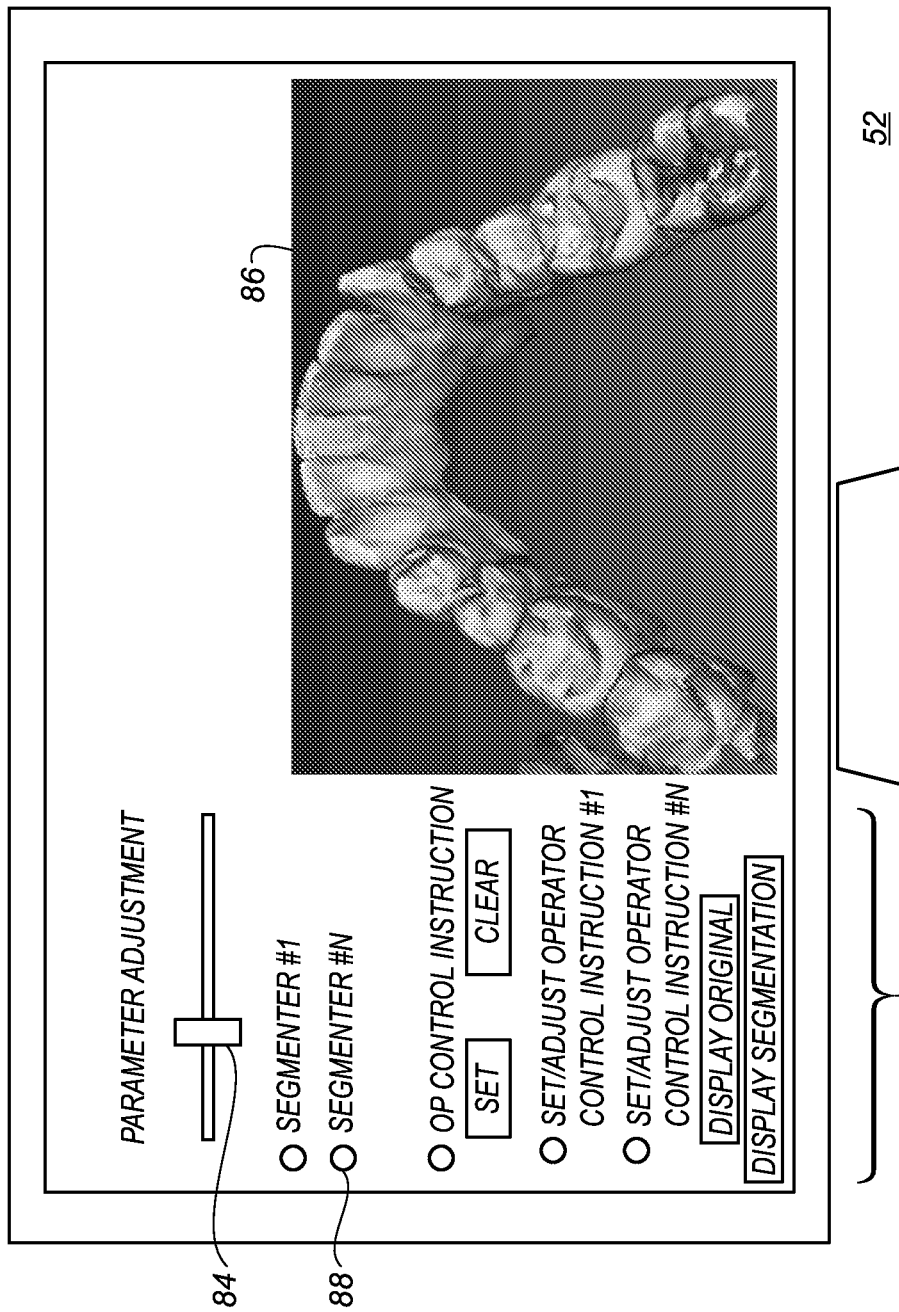

FIGS. 9A-9C show operator interface screens 52 for portions of a sequence for review and entry of markup instructions for refining mesh segmentation processing according to certain exemplary embodiments of the present disclosure. Interim mesh segmentation results are shown in a display area 86 on screen 52. A number of controls 90 for adjustment of the segmentation process are available, such as an adjustment control 84 for setting a level for overall aggressiveness or other parameter or characteristic of the segmentation processing algorithm. Optional selection controls 88 allow the viewer to specify one or more segmentation algorithms to be applied. This gives the operator an opportunity to assess whether one particular type of segmentation algorithm or another appear to be more successful in performing the segmentation task for the given mesh digital model. The operator can compare results against the original and adjust parameters to view results of successive segmentation attempts, with and without operator markup.

FIG. 9A also shows a trace pattern 96 that is entered as an operator seed line instruction for correcting or refining segmentation processing, as was shown previously with respect to FIG. 8A. According to an embodiment of the present disclosure, an operator mark in the form of trace pattern 96 or other arbitrary marking/geometric can be used to provide seed points that indicate a specific feature for segmentation, such as a molar or other tooth feature that may be difficult to process for conventional segmentation routines. Seed marks can then be used as input to a fast marching algorithm or other algorithm type, as described previously. In some cases, for example, adjacent teeth may not be accurately segmented with respect to each other, operator markup can provide useful guidance for segmentation processing where standard segmentation logic does not perform well. As FIG. 9A shows, the operator can have controls 90 available that allow the entered markup to be cleared or provided to the segmentation processor. As FIG. 9B shows, color or shading can be used to differentiate various teeth or other structures identified by segmentation. Additional controls 90 can also be used to display individual segmented elements, such as individual teeth, for example. As FIG. 9C highlights, in some exemplary embodiments, individual controls 90 can be used individually or in combination.

In one embodiment, segmentation of individual teeth from each other can use curvature thresholds to compute margin and border vertices, then use various growth techniques to define the bounds of each tooth relative to margin detection.

In some exemplary embodiments, controls 90 can include, but are not limited to enter/adjust seed or boundary geometrics, enter/adjust selected segmentation procedures, enter/adjust number of objects to segment, subdivide selected object, modify segmented object display, etc.

The segmentation that is provided using structured light illumination and detection can be correlated with 3D image results obtained from CBCT or other radiographic method for volume image reconstruction. By combining the tooth structure data for visible portions of the tooth structure with the reconstructed CBCT volume data, an accurate characterization of the anatomy can be obtained, without the need for further exposure of the patient to ionizing radiation.

Figure 10:
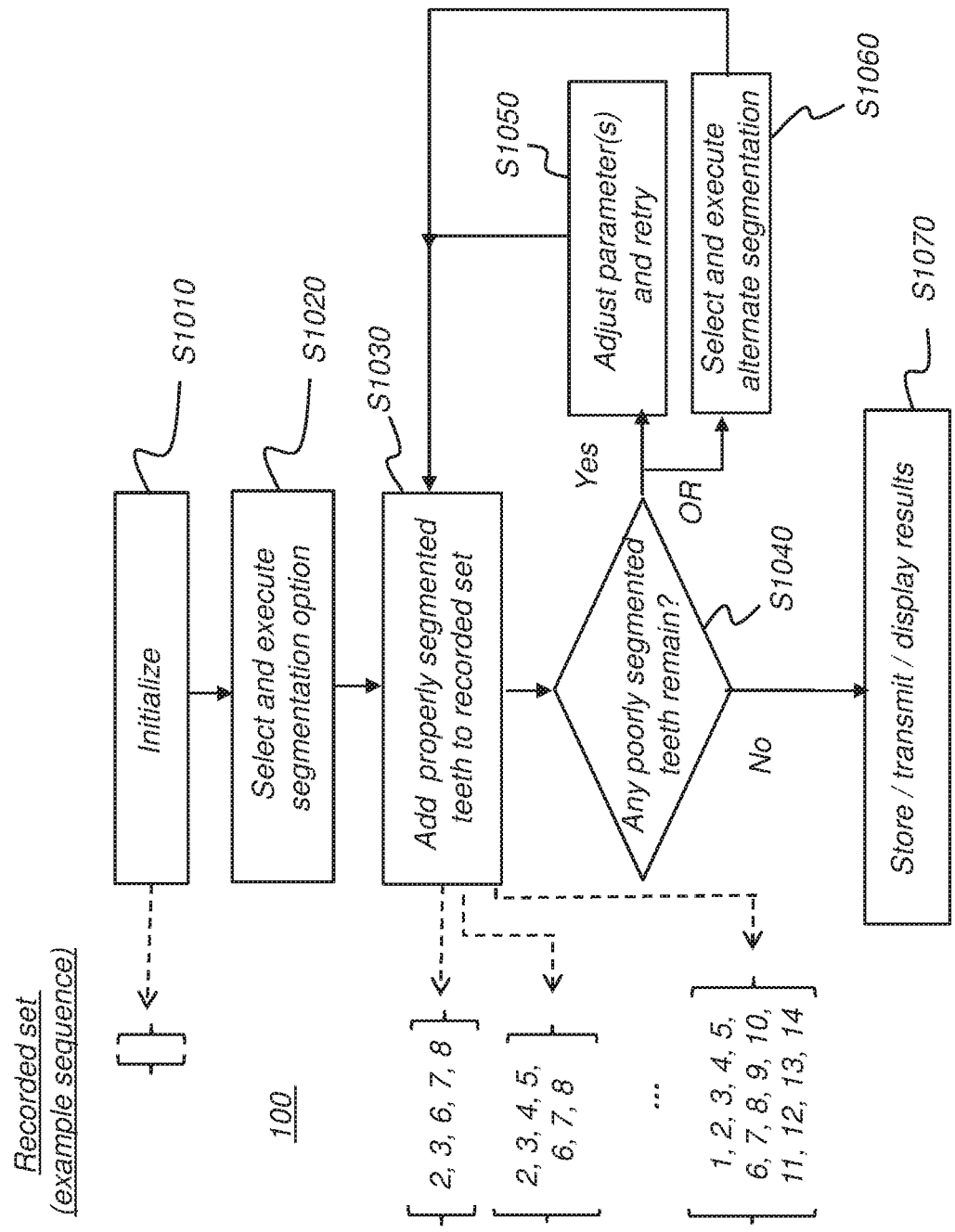
FIG. 10 is a logic flow diagram that shows steps in iterative execution of segmentation.

Certain exemplary method and/or apparatus embodiments of the present disclosure can provide iterative segmentations that allow the practitioner to utilize different segmentation methods/algorithms in an efficient manner. As noted previously, different segmentation methods are available; each method has its strengths and shortcomings for effective characterization of the visible tooth structure. A logic flow diagram of FIG. 10 shows exemplary imaging method embodiments that allow the practitioner to take advantage of successive segmentation techniques in constructing a set of well-segmented teeth, so that a full dental arch can be efficiently characterized. By identifying successful segmentation results as different methods are executed, the practitioner can record individual teeth that are properly segmented and eliminate them from further segmentation processing that could otherwise compromise successful results and complicate the segmentation task.

In one exemplary method and/or apparatus embodiment, after a first exemplary segmentation, individual teeth that are properly segmented (e.g., segmentation factor or segmentation characteristic (e.g., determined by the processor) is sufficient) can be automatically removed or eliminated from further/subsequent segmentation(s) or a second segmentation applied to remaining portions of the 3D mesh (e.g., teeth).

Referring to the FIG. 10 sequence, the task of the segmentation process is to construct, in an iterative and interactive manner, a recorded set 100 of well-segmented teeth from a 3-D digital mesh model of the patient's dentition. This can include the full dental arch, as shown in the example that follows; alternately, the full recorded set 100 can include only a partial portion of the dental arch that is of interest for a particular patient. In the terminology used in the following description, the logic flow iteratively identifies and "records" well-segmented teeth and thus "removes" them from the "3-D digital mesh model" that is actively being processed. In this way, subsequent segmentation processing works with a reduced set of un-segmented structures, correspondingly reducing the number of calculations and/or overall complexity of the segmentation problem as processing continues.

The segmentation procedure shown in FIG. 10 starts with an initialization step S1010 that begins with the obtained 3-D mesh model and a recorded set 100 that is, initially, an empty set { } for listing properly segmented teeth and for removing these properly segmented teeth from further segmentation processing. In a segmentation step S1020, the practitioner selects a first segmentation algorithm for initial segmentation of the 3-D mesh, after the execution of the scan sequence using intraoral camera 24 (FIG. 1). An exemplary first segmentation is the automatic segmentation as illustrated by step S202 in FIG. 6B.

Figure 11:
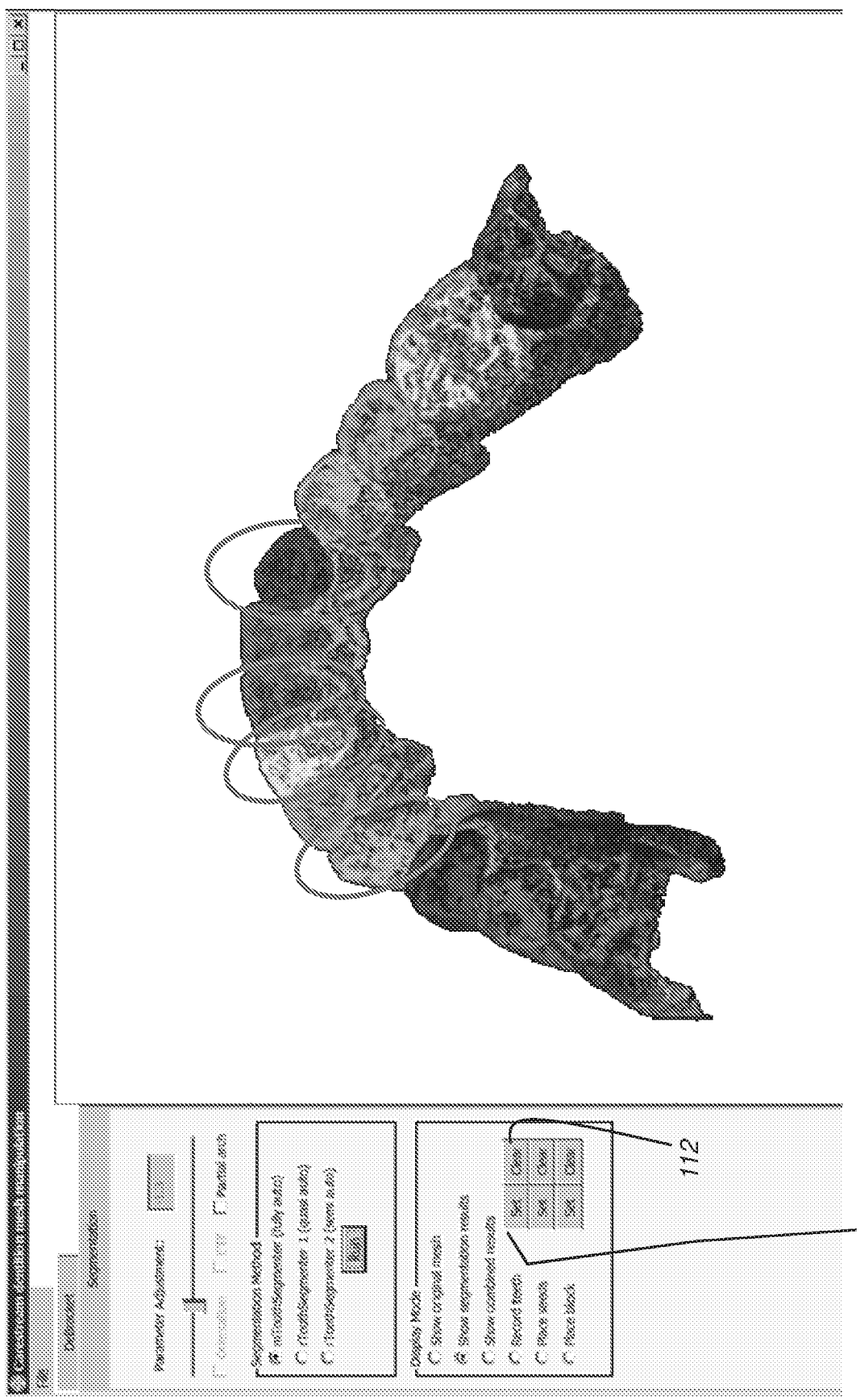
FIG. 11 shows a display showing a possible segmentation of portions of the dental arch.

The segmentation results from step S1020 in FIG. 10 can display to the practitioner as shown in the example screen of FIG. 11. Segmented areas of the teeth can appear in color or grayscale values that highlight the segmented tooth areas within the mesh. A number of teeth in the arch are well-segmented in this example; these well-segmented teeth can be recorded and removed from the 3-D mesh model that requires further processing. Other teeth may not be well-segmented, such as those shown having perceptible gaps and other errors. As part of a recording step S1030, the practitioner uses a touch screen, mouse, or other pointer or keyboard entry to highlight or otherwise indicate well-segmented teeth. With one or more teeth selected and highlighted, the practitioner then enters a Set instruction 110 or other operator instruction that adds the well-segmented teeth to the recorded set 100, as described previously. This can include commands to set and unset a particular segmentation, for example. In terms of the processing sequence of FIG. 10, the Set instruction 110 records each of the specified segmented teeth in set 100 and effectively removes the recorded teeth from the 3-D mesh model, thereby forming a modified 3-D mesh model. Teeth in the recorded set 100 are considered to be well-segmented and are thus removed from further segmentation processing.

Subsequent iterative processing can then focus on the smaller group of teeth that remain in the 3-D mesh model and that have not been successfully segmented by the initial segmentation algorithm. Iteratively reducing the size of the poorly-segmented data within the 3-D mesh model helps to reduce processing time and complexity and allows adjustment or change of the segmentation method and use of more specialized or more interactive segmentation techniques to be used on the smaller subset of teeth that still require processing. With each iteration, a modified segmentation procedure is identified or defined for use in processing what remains in the modified 3-D mesh model. As described in more detail subsequently, the segmentation procedure can make use of a different algorithm or may use a similar algorithm with adjusted parameters, such as changed threshold values for example.

In the example of FIG. 11, some of the teeth in the arch can be added to recorded set 100 in step S1030 (FIG. 10) and thus eliminated from further 3-D mesh processing. Other teeth have not yet been satisfactorily segmented and require additional processing for proper segmentation. A number of poorly segmented teeth are circled in the example of FIG. 11. The poorly segmented teeth in FIG. 11 have errors such as inaccurate margin lines.

An interactive process can be used for identifying well-segmented teeth that can be added to recorded set 100 in recording step S1030. In the example of FIG. 11, the practitioner, upon examining segmentation results tooth-by-tooth, selects and highlights the teeth that show acceptable segmentation, such as using a touch screen or other pointer. The practitioner then enters a Set instruction 110 that records each successfully segmented tooth, thus adding the tooth to the recorded set 100 as shown with reference to FIG. 10, removing the tooth from the active 3-D mesh being processed. For subsequent processing of poorly segmented teeth, the practitioner may respond to system prompts to enter seed points or other markings, as described with reference to step S216 in FIG. 6B, to assist in more successful segmentation.

Continuing with the FIG. 10 sequence, a test step S1040 provides the practitioner with a number of options for the remaining teeth, depending on the success or failure of the segmentation strategy that has been applied. One option is to execute a parameter adjustment step S1050 to obtain the modified segmentation procedure, then to retry segmentation on the teeth not yet recorded using adjusted parameter settings with the exemplary primary assisted segmentation algorithm indicated in Step S206. Thus, for example, the practitioner can set an adjustment level to a different value for a more or less "aggressive" segmentation processing or can adjust thresholds that determine classification of features. Another option is an alternate execution step S1060. For step S1060, the practitioner selects a different segmentation technique for teeth not yet suitably segmented. This can include a segmentation method that requires additional operator interaction, so that automated processing S202 is used to segment the bulk of the teeth, with specialized processing S206 and markup S216 by the practitioner for processing teeth that do not respond as well to automated segmentation processing. As shown in FIG. 10, a display step S1070 executes at the end of segmentation processing, allowing the practitioner to view a displayed image and to store or transmit processing results as needed.

It should also be noted that one or more teeth that have been segmented can be "cleared" and restored or returned to the 3-D mesh model using a Clear instruction 112 (FIG. 11). Thus, for example, the viewer may determine that results for a particular tooth are not satisfactory or can be improved and that additional segmentation procedures would be helpful. Restoring a specified tooth to the modified 3-D mesh model allows further processing of the tooth in subsequent segmentation operations, either using different segmentation algorithms or applying different values to segmentation variables.

Figure 12:
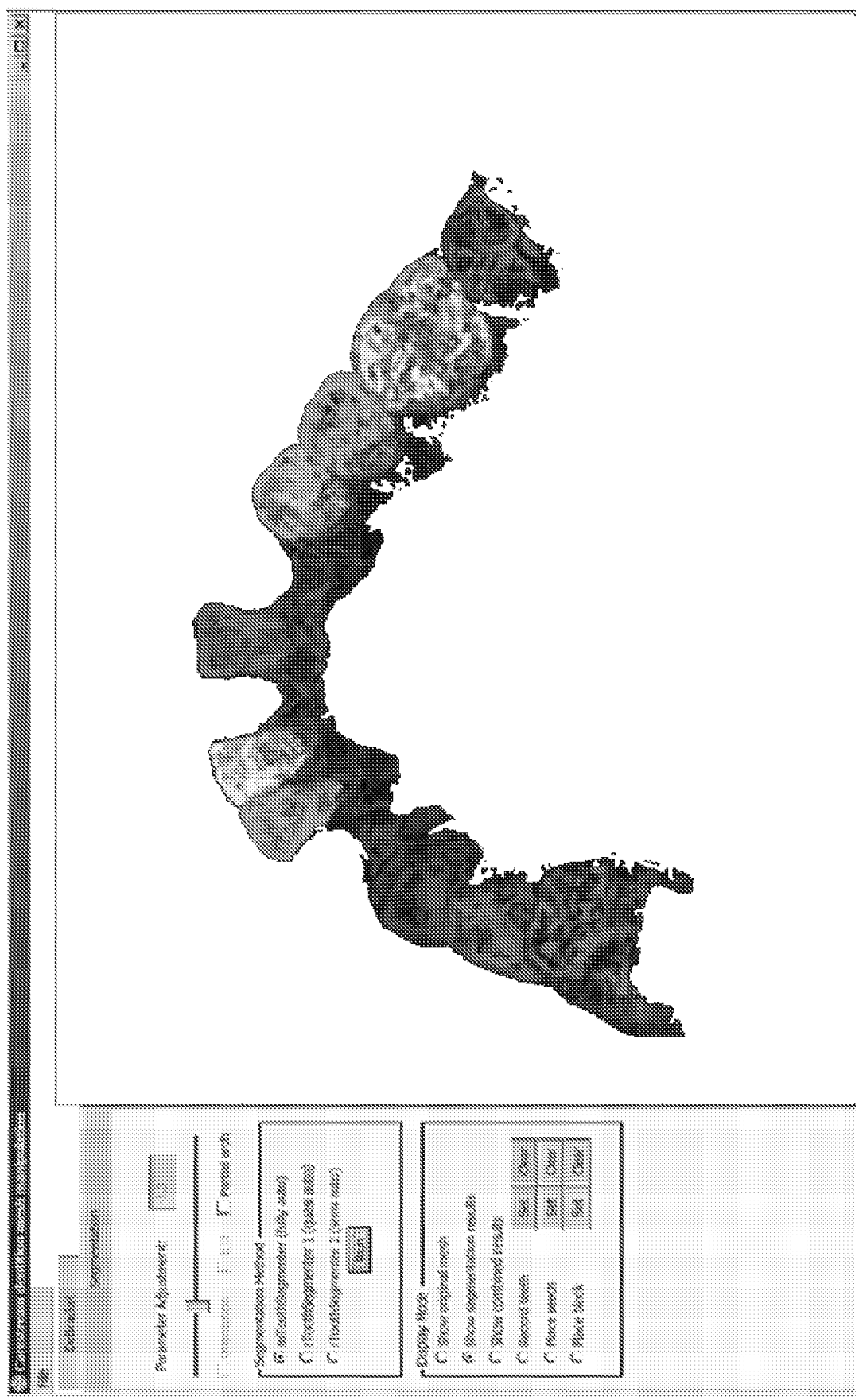
FIG. 12 shows a set of well-segmented teeth from the example segmentation of FIG. 11.
Figure 13:
FIG. 13 shows segmentation results following parameter adjustment by the viewing practitioner.
Figure 14:
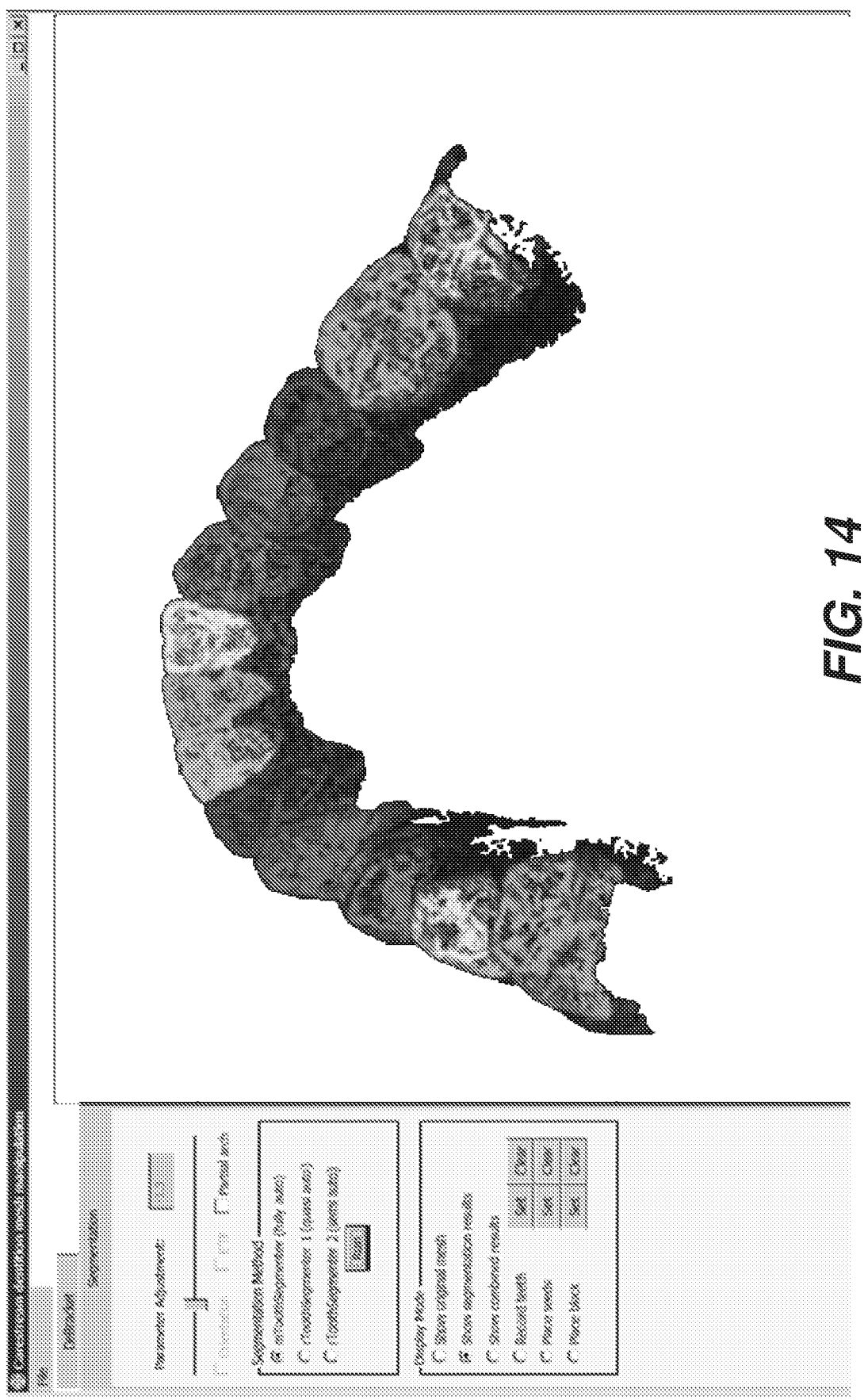
FIG. 14 shows complete segmentation results for the full dental arch, obtained using the process described herein.

By way of example, FIG. 12 shows a set of well-segmented teeth from the example segmentation of FIG. 11 (e.g., that are removed from further segmentation iterations/processing). FIG. 13 shows segmentation results following parameter adjustment and subsequent segmentation of the four poorly segmented teeth of FIG. 11, as described previously with reference to step S1050, which are now more accurately segmented. For example, in FIG. 13 the margin lines are more accurate. FIG. 14 shows complete segmentation results for the full dental arch, obtained using the process described with reference to FIG. 10. In this example, FIG. 14 shows the well segmented recorded teeth from a first segmentation (e.g., FIG. 11) with well segmented recorded teeth from a second segmentation (e.g., FIG. 13).

In certain exemplary method and/or apparatus embodiments, sufficiently segmented teeth can be automatically removed from additional segmentations that are run before mesh segmentation results (e.g., interim mesh segmentation results shown in the display area 86 or final segmentation results) are displayed to the user. In such exemplary embodiments, individual teeth that are properly segmented after a first segmentation is performed on a 3D mesh can be automatically removed or eliminated from further/subsequent segmentation(s) or a second segmentation applied to remaining portions of the 3D mesh (e.g., teeth). In one exemplary embodiment, a confidence factor threshold can be used to remove segmented teeth (e.g., portions) from the 3D mesh. Such a confidence factor threshold can be preset, variable and/or set by the user. Exemplary confidence factors can be computed based on one or more technical metrics such as but not limited to the probability distribution function (PDF) of a segmented tooth surface normals and/or exemplary morphological descriptor of the boundaries of a segmented tooth. The PDF of surface normals can be practically computed as the normal histogram as an exemplary technology. The morphological descriptor of the boundaries can be computed using an exemplary computer vision technology named chain coding. Other technical metrics known in the dental image processing art can be used. Alternative confidence factors can be weighted combination of such technical metrics and/or scaled to a prescribed range such as a range between 0 to 1.

Figure 15A:
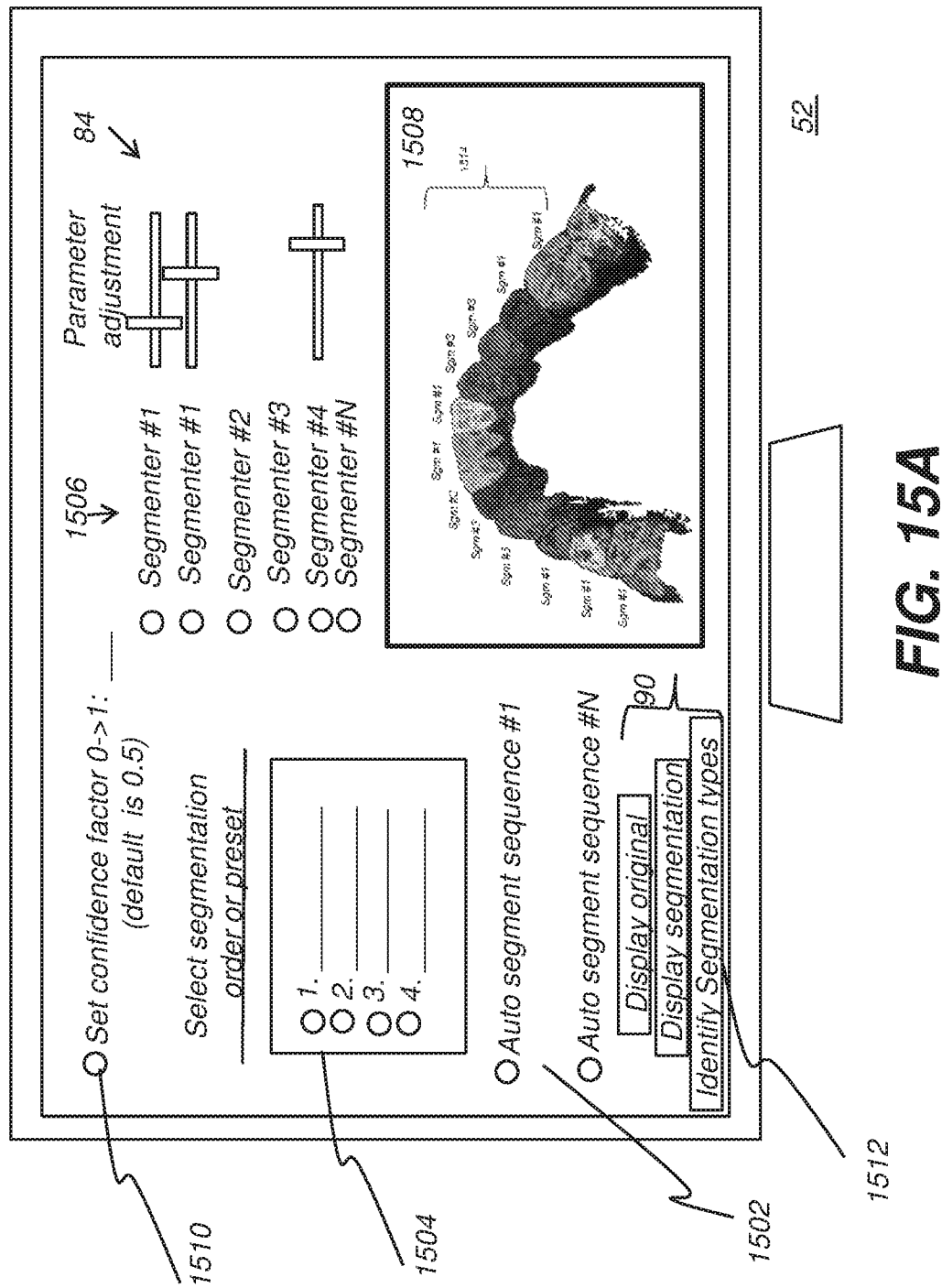
FIGS. 15A-15B are diagrams that shows an exemplary user interface with controls to preset and/or change an order for sequential segmentations successively used in automatic segmentation methods/apparatus according to certain embodiments of the present disclosure.
Figure 15B:
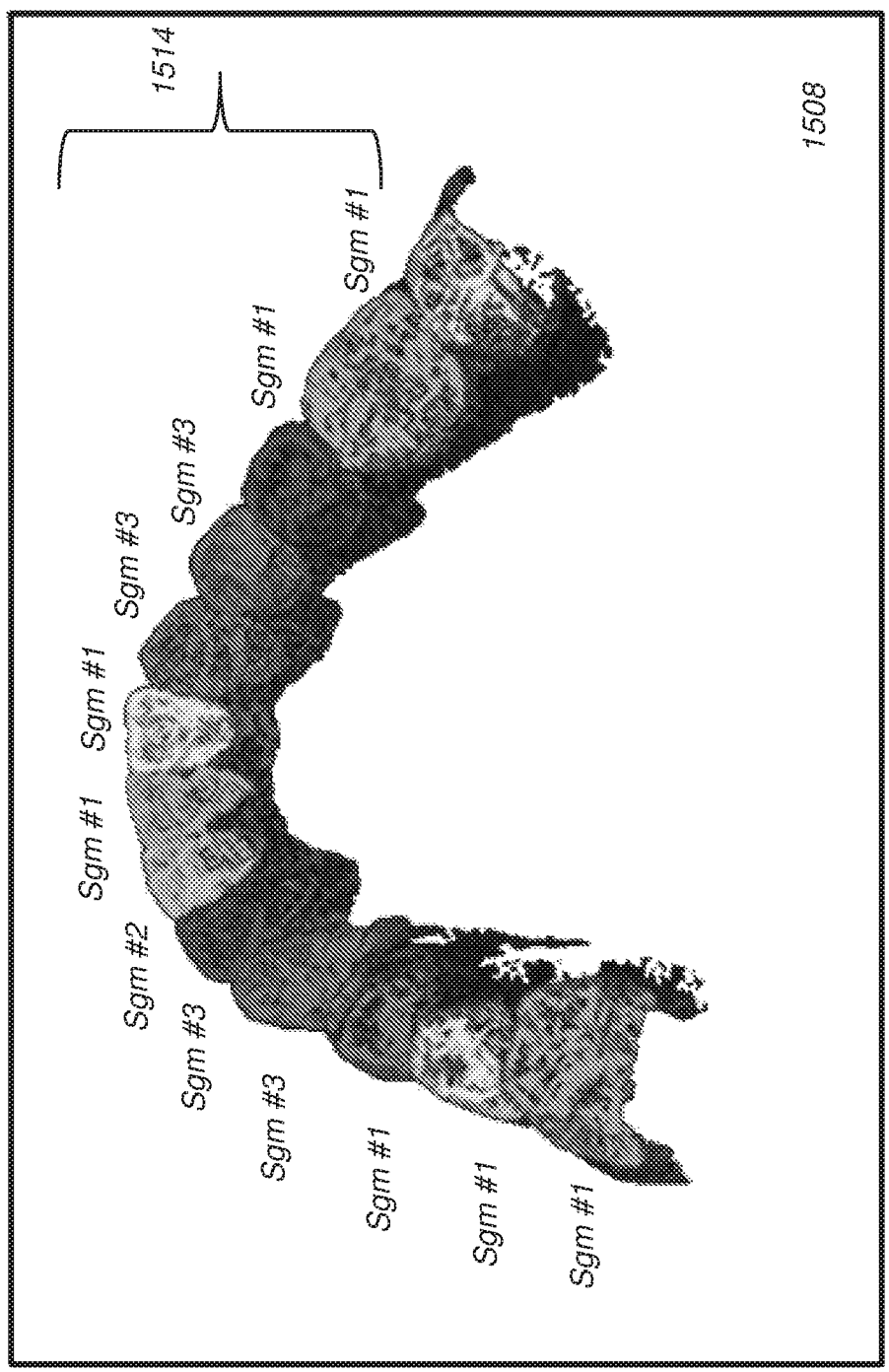

FIGS. 15A-15B are diagrams that shows an exemplary user interface with controls to preset and/or change an order for sequential segmentations successively used in an automatic segmentation process. Each successive segmentation in certain exemplary automatic segmentation embodiments can record and then remove teeth segmented with a confidence factor over a threshold from further segmentation. The complete segmentation results for the full dental arch (or portion thereof) can be displayed when all individual teeth are recorded. Alternatively, the complete segmentation results for the full dental arch (or portion thereof) can be displayed when all segmentations have been run and any teeth that were not recorded (and removed) can be indicated for the practitioner.

As shown in FIG. 15A, a preset sequence 1502 of segmentation types can be selected or the practitioner can set a desired order 1504 of segmentation types selected from a library or plurality of segmentation types 1506. Again, the adjustment control 84 can be used to set a level for overall aggressiveness or other parameter(s) or characteristic(s) of a specific segmentation processing algorithm type among segmentation types 1506. In one exemplary embodiment, the confidence factor 1510 can be optional and capable of adjustment by the practitioner. In one exemplary embodiment, operator controls 90 can be used to display to the practitioner the complete segmentation results. An optional window 1508 can be used to display the original 3D mesh or the segmented result or the segmented result with segmentation types actually used. For example, operator control 1512 can be used to display to the practitioner the complete segmentation results for the full dental arch (or portion thereof) when all segmentations have been run with the segmentation type 1514 highlighted for each recorded tooth as shown in FIG. 15B.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as control logic processors as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can allow the practitioner to take advantage of successive segmentation techniques to remove properly segmented dentition from subsequent different segmentation attempts in constructing a set of well-segmented teeth from a dentition 3D mesh model. In one exemplary embodiment, operator controls can be used to display to the practitioner segmentation types that recorded each tooth in the complete automatic segmentation results. Although embodiments of the present disclosure are illustrated using dental imaging apparatus, similar principles can be applied for other types of diagnostic imaging and for other anatomy. Exemplary embodiments according to the application can include various features described herein (individually or in combination).

In one exemplary embodiment, an apparatus for intraoral imaging xan include a structured light imaging camera that is configured to acquire a 3-D mesh model of a patient's dentition, and a computer processor in signal communication with the imaging camera and with a display and that is programmed with instructions for: executing a first segmentation procedure on the obtained 3-D mesh model and displaying one or more segmented teeth from the 3-D mesh model, recording at least one of the one or more segmented teeth according to operator instruction and removing the recorded at least one tooth from the 3-D mesh model to form a modified 3-D mesh model, repeating, one or more times, a sequence of: (i) identifying a modified segmentation procedure, (ii) executing the modified segmentation procedure on the modified 3-D mesh model and displaying one or more segmented teeth from the modified 3-D mesh model, and (iii) recording at least one of the one or more segmented teeth and removing the recorded at least one tooth from the modified 3-D mesh model, and displaying, storing, or transmitting recorded segmentation results.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A computer-implemented hybrid method for segmenting at least a portion of an unsegmented 3-D teeth model and generating one or more segmented 3-D teeth models from the portion of the unsegmented 3-D teeth model, the method comprising the steps of:
    obtaining a 3-D mesh model of a patient's dentition;
    executing a tooth segmentation procedure on the 3-D mesh model to identify one or more portions of the 3-D mesh model corresponding respectively to one or more teeth of the patient's dentition from other portions of the 3-D mesh model and displaying the one or more identified teeth;
    recording the one or more identified teeth according to an operator instruction;
    removing the one or more portions of the 3-D mesh model corresponding respectively to the one or more identified teeth from the 3-D mesh model to form a modified 3-D mesh model;
    performing, one or more times, a sequence of steps including:
        (i) identifying a subsequent tooth segmentation procedure the same as or different from a prior tooth segmentation procedure;
        (ii) executing the subsequent tooth segmentation procedure on the modified 3-D mesh model to identify one or more portions of the modified 3-D mesh model corresponding respectively to one or more teeth of the patient's dentition previously unidentified from other portions of the modified 3-D mesh model and displaying the previously unidentified one or more teeth;
        (iii) recording the previously unidentified one or more teeth; and
        (iv) removing the one or more portions of the modified 3-D mesh model corresponding respectively to the one or more previously unidentified teeth from the modified 3-D mesh model; and
    displaying, storing, or transmitting the recorded teeth as segmentation results.

2. The method of claim 1 wherein the segmentation results distinguish one or more teeth from the patient's gum tissue.

3. The method of claim 1 wherein the segmentation results distinguish individual teeth from each other.

4. The method of claim 1 wherein the operator instruction for recording identifies a displayed tooth according to a touch screen or computer mouse selection.

5. The method of claim 1 wherein the operator instruction verifies a tooth segmentation result.

6. The method of claim 1 wherein the step of performing is terminated by an operator instruction.

7. The method of claim 1 wherein the operator instruction adds one or more geometric primitives for interactive tooth segmentation.

8. The method of claim 1 wherein the step of obtaining the 3-D mesh model comprises acquiring a plurality of structured light images from a hand-held intraoral camera.

9. The method of claim 1 wherein one of the tooth segmentation procedures comprises an automatic segmentation procedure, and wherein the results of the automatic segmentation procedure appear in color.

10. The method of claim 1 further comprising restoring one or more of the recorded teeth to the modified 3-D mesh model.

11. A computer-implemented method for generating a digital model of intraoral features, the method comprising the steps of:
    generating a 3-D digital mesh model of a patient's dentition from a plurality of structured light images;
    performing automatic tooth segmentation on the generated 3-D digital mesh model;
    displaying segmentation results from automatic tooth segmentation and recording a set of one or more automatically segmented teeth in response to an operator instruction;
    accepting at least a second operator instruction related to an interactive segmentation of other teeth not in the recorded set;
    performing the interactive segmentation of a portion of the 3-D digital mesh model corresponding to other teeth not in the recorded set and recording one or more interactively segmented teeth in the recorded set; and
    displaying, storing, or transmitting recorded segmentation results from the recorded set.

12. The method of claim 11 wherein the second operator instruction identifies an error in the displayed segmentation results from the automatic tooth segmentation.

13. The method of claim 11 further comprising a step of returning at least one recorded tooth back to the 3-D digital mesh model before an additional segmentation of the 3-D digital mesh model is performed.

14. An apparatus for intraoral imaging, said apparatus comprising:
    a structured light imaging camera that is configured to acquire a 3-D mesh model of a patient's dentition; and
    a computer processor in signal communication with the imaging camera and with a display, said computer processor being programmed with instructions for:
    executing a segmentation procedure on the acquired 3-D mesh model to identify a plurality of segmented teeth from the acquired 3-D mesh model;
    recording at least one of the plurality of segmented teeth to remove at least one already segmented tooth from the 3-D mesh model to form a modified 3-D mesh model;
    performing, until a desired portion of the plurality of segmented teeth are recorded, a sequence including the steps of:
        (i) selecting a different segmentation procedure;
        (ii) executing the different segmentation procedure on the modified 3-D mesh model; and
        (iii) recording at least one newly segmented tooth of one or more segmented teeth from the different segmentation procedure and removing the recorded at least one newly segmented tooth from the modified 3-D mesh model; and displaying, storing, or transmitting the plurality of recorded segmented teeth from the modified 3-D mesh model.

15. The apparatus of claim 14, where the recorded segmented teeth are recorded and removed from the 3-D mesh model or the modified 3-D mesh model when a segmenting confidence factor is above a prescribed threshold.

* * * * *